(12) United States Patent
Jiao et al.

(10) Patent No.: US 6,828,312 B2
(45) Date of Patent: Dec. 7, 2004

(54) PHARMACEUTICALLY ACTIVE COMPOUNDS AND METHODS OF USE THEREOF

(75) Inventors: Jin-An Jiao, Weston, FL (US); Lawrence K. Luepschen, Miami, FL (US); Esperanza Nieves, Plantation, FL (US); Hing C. Wong, Weston, FL (US); Dean P. Taylor, Weston, FL (US)

(73) Assignee: Sunol Molecular Corporation, Miramar, FL (US)

( * ) Notice: Subject to any disclaimer, the term of this patent is extended or adjusted under 35 U.S.C. 154(b) by 0 days.

(21) Appl. No.: 09/406,269

(22) Filed: Sep. 24, 1999

(65) Prior Publication Data

US 2002/0065327 A1 May 30, 2002

Related U.S. Application Data

(60) Provisional application No. 60/101,887, filed on Sep. 25, 1998.

(51) Int. Cl.[7] .................. A61K 31/66; A61K 31/675
(52) U.S. Cl. ............................... 514/102; 514/79
(58) Field of Search .................. 514/75, 79, 83, 514/84, 85, 90, 102, 126, 127, 129, 130

(56) References Cited

U.S. PATENT DOCUMENTS

| | | | |
|---|---|---|---|
| 5,006,515 A | * 4/1991 | Schwab et al. | 514/89 |
| 5,403,829 A | * 4/1995 | Lehtinen et al. | 514/102 |
| 5,728,650 A | 3/1998 | Fisher et al. | 504/195 |
| 5,854,227 A | * 12/1998 | Hartmann et al. | 514/79 |

FOREIGN PATENT DOCUMENTS

| | | |
|---|---|---|
| WO | WO 91 05791 | 5/1991 |
| WO | WO 97 09063 A | 3/1997 |
| WO | WO 98 40408 A | 9/1998 |
| WO | WO 99 03498 | 1/1999 |

OTHER PUBLICATIONS

CA:134:37031 abs of WO 2000077246 Dec. 2000.*
CA:139:149413 abs of WO 2003061567 Jul. 2003.*
Journal of Medicinal Chem by Ksander et al 37 pages 1823–1832 1994.*
CA:107:59121 abs of J Med Chem. by Nguyen et al 30(8) pp 1426–1433 1987.*
CA:121:179868 abs of WO 9407501 Apr. 14, 1994.*
CA;123:33653 abs of EP 623625 Nov. 9, 1994.*
CA:99:212705 abs of DE 3203307 Jul. 28, 1983.*
CA:124:45717 abs of JP07242538, Sep. 1995.*
CA:125:212249 abs of Blood Coagulation Fibrinolysis by Harenberg et al 7(4) pp 477–463, 1996.*
CA:130:209820 abs of DE 19738005, Mar. 1999.*
CA:127:5356 abs of WO9715598, May 1997.*
CA:126:324966 abs of Res Virol by Grimaldi et al 148(2) pp 177–180, 1997.*
CA:125:320562 abs of WO9631124, Apr. 1996.*
CA: 119:28231 abs of Bioorg Med Chem Lett by Fletcher et al 3(2) pp 141–146, 1993.*
CA:120:219245 abs of Macromolecules by Chan 27(8) pp 2159–2164, 1994.*
Chemical Abstracts, vol. 93, No. 25, Abstract No. 239522 (1980).

* cited by examiner

*Primary Examiner*—Jean F. Vollano

(57) ABSTRACT

The invention includes pharmaceutically active compounds and methods of treatment and pharmaceutical compositions that utilize or comprise one or more such compounds. Compounds of the invention are particularly useful for treatment or prophylaxis of undesired thrombosis.

5 Claims, 10 Drawing Sheets

TF/VIIa-dependent Factor X Activation

TF/VIIa/phospholipids/$Ca^{++}$ + DMSO (diluted DMSO or Buffer) or Compound 15 min at 37 C Add FX Add EDTA Add FXa Substrate Add 50% Acetic Acid Read OD at 405nm Table 1

| Compounds | % Inhibition of FXa Activity at | | % Inhibition of FVIIa Activity at | | % Inhibition of Thrombin Activity at | | % Inhibition of Trypsin Activity at | |
|---|---|---|---|---|---|---|---|---|
| | 714 µM | 71 µM | 833 µM | 83 µM | 625 µM | 63 µM | 625 µM | 63 µM |
| Compound 2 | 3 | 3 | 27 | 5 | 57 | -16 | -8 | -16 |
| Compound 1 | 7 | 1 | 42 | 1 | 41 | -9 | -2 | 10 |

Compounds were in DMSO and were diluted with 10 mM Hepes-NaOH, pH 7.5 if necessary

FIG. 2A

Table 2

| Compounds | % Inhibition of FX Activation Catalyzed by | | | |
|---|---|---|---|---|
| | TF/VIIa | RVV | FIXa | FVIIa |
| Compound 2 | | | | |
| 96 μM | nd" | 6.1 | 23.2 | nd |
| 32 μM | 94.5 | 1.8 | 6.8 | nd |
| Compound 1 | | | | |
| 100 μM | nd | nd | nd | 6.0 |
| 96 μM | nd | 5.0 | 21.7 | nd |
| 32 μM | 85.0 | 4.9 | 0.0 | nd |

$nd^2$ . not determined.

The compounds were in DMSO and were diluted with 10 mM Hepes-NaOH.pH 7.5 if necessary

FIG. 2B

Table 3

| Compound Concentrations (µM) | % Inhibition by Compound 2 | % Inhibition by Compound 1 |
|---|---|---|
| 0 | 0 | 0 |
| 2 | 6 | 1 |
| 4 | 10 | 7 |
| 8 | 45 | 14 |
| 16 | 62 | 42 |
| 32 | 84 | 83 |
| 48 | 92 | 91 |
| 96 | 96 | 94 |

Compounds 1 and 2 were dissolved in 0.1 M NaOH, then diluted to 16.5 mM NaOH with water. The compounds were preincubated with TF/VIIa for 15 minutes at 37 C prior to addition of FX. Following FX addition, the reaction was incubated for 15 minutes at 37 C.

FIG 2C

Table 4

| Compound Concentrations (μM) | % Inhibition by Compound 2 | % Inhibition by Compound 1 |
|---|---|---|
| 0 | 0 | 0 |
| 2 | 24.7 | -0.3 |
| 4 | 39.9 | 20.8 |
| 8 | 67.2 | 26.9 |
| 16 | 79.4 | 61.1 |
| 32 | 87.5 | 84.5 |
| 48 | | 90.3 |
| 96 | | |

Compounds 1 and 2 were in DMSO and diluted with 10 mM Hepes-NaOH. pH 7.5

FIG. 2D

| Compounds | Factor X Activation IC$^{50}$ in µM | Factor IX Activation IC$^{50}$ in µM | FXa Activity % Inhibitors @ 83 µM | FVIIa Activity % Inhibitors @ 83 µM | Thrombin Activity % Inhibitors @ 63 µM | Trypsin Activity % Inhibitors @ 71 µM |
|---|---|---|---|---|---|---|
| Compound 1 | 10 | 26 | 4 | 1 | 0 | 4 |
| Compound 2 | 6.5 | 55 | 3 | 5 | 0 | 0 |
| Compound 3 | 70 | n.d. | n.d. | n.d. | n.d. | n.d. |
| Compound 4 | >200 | n.d. | n.d. | n.d. | n.d. | n.d. |
| Compound 5 | 100 | n.d. | n.d. | n.d. | n.d. | n.d. |
| Fosamax | 80 | n.d. | n.d. | n.d. | 0 | n.d. | n.d. – not determined

FIG. 3

| Compounds | PT Clotting Time (Seconds) | APTT Clotting Time (Seconds) |
|---|---|---|
| Control (DMSO) | 37.0 | 29.4 |
| Compound 1 (167µM) | 75.3 | 35.4 |
| Compound 2 (167µM) | 76.8 | 33.0 |

FIG. 4

| Compound | Km for FX (nM) |
|---|---|
| Control (DMSO) | 19 |
| 10 µM - compound 1 (in DMSO) | 37 |
| 20 µM - compound 2 (in DMSO) | 76 |

FIG. 5

PHARMACEUTICALLY ACTIVE COMPOUNDS AND METHODS OF USE THEREOF

CROSS-REFERENCE TO RELATED APPLICATION

The present application claims the benefit of U.S. Provisional Application No. 60/101,887 filed on Sep. 25, 1998, the disclosure of which is hereby incorporated by reference.

BACKGROUND OF THE INVENTION

1. Field of the Invention

The present invention relates to pharmaceutically active compounds and more particularly to pharmaceutical compositions that utilize or comprise one or more of such compounds. Preferred compounds are especially useful for the treatment or prophylaxis of undesired thrombosis. Also included are methods for treating thrombosis. The invention has a wide spectrum of applications including use in screening candidate compounds for the treatment or prophylaxis of thrombosis.

2. Background

Blood clotting assists hemostasis by minimizing blood loss. Generally, blood clotting is initiated by vessel damage and requires platelet aggregation, coagulation factors and inhibition of fibrinolysis. The coagulation factors act through a cascade that relates the vessel damage to formation of a blood clot (see generally L. Stryer, *Biochemistry*, 3rd Ed, W.H. Freeman Co., New York; and A. G. Gilman et al., *The Pharmacological Basis of Therapeutics*, 8th Edition, McGraw Hill Inc., New York, pp. 1311–1331).

Tissue factor (TF), an integral membrane protein of 263 amino acids, is responsible for initiating the coagulation protease cascade. Vascular damage exposes blood to tissue factor expressed on subendothelial cell surfaces, leading to the formation of a calcium-dependent, high-affinity complex with the plasma factor VII (FVII) or activated factor VII (FVIIa). Binding to TF promotes rapid proteolytic cleavage of the zymogen FVII to the active serine protease FVIIa by a number of proteases such as factor Xa, or thrombin. TF also functions as an essential cofactor for FVIIa by dramatically enhancing the catalytic efficiency of FVIIa for its protein substrates factors IX and X. TF/VIIa complex activates factors IX (FIX) and X (FX) via limited proteolysis, ultimately leading to thrombin generation and fibrin deposition. Under pathological conditions such as atherosclerosis or following invasive surgical procedures such as microvascular graft, angioplasty, deployment of an implanted device (e.g., a stent, catheter or arteriovenous shunt), or endarterectomy, TF-initiated coagulation can lead to thrombotic disorders that can result e.g. in heart attack, stroke, unstable angina or other coronary disorder.

Thrombosis also may accompany various thromboembolic disorders and coagulopathies such as a pulmonary embolism (e.g., atrial fibrillation with embolization, deep vein thrombosis, etc.) and disseminated intravascular coagulation, respectively. Manipulation of body fluids can also result in an undesirable thrombus, particularly in blood transfusions or fluid sampling, as well as procedures involving extracorporeal circulation (e.g., cardiopulmonary bypass surgery) and dialysis.

Certain anti-coagulants have been used to alleviate or avoid blood clots associated with thrombosis. Blood clotting often can be minimized or eliminated by administering a suitable anti-coagulant or mixture thereof, including one or more of a coumarin derivative (e.g., warfarin and dicumarol) or a charged polymer (e.g., heparin, hirudin or hirulog). See e.g., Gilman et al., supra, R. J. Beigering et al., *Ann. Hemathol.*, 72:177 (1996); J. D. Willerson, *Circulation*, 94:866 (1996).

Certain antibodies with anti-platelet activity have also been used to alleviate various thromboses. For example, ReoPro™ is a therapeutic antibody that is routinely administered to alleviate various thromboembolic disorders such as those arising from angioplasty, myocardial infarction, unstable angina and coronary artery stenoses. Additionally, ReoPro™ can be used as a prophylactic to reduce the risk of myocardial infarction and angina (J. T. Willerson, *Circulation*, 94:866 (1996); M. L. Simmons et al., *Circulation*, 89:596 (1994)).

However, use of prior anti-coagulants is often associated with side effects such as hemorrhaging, re-occlusion, "white-clot" syndrome, irritation, birth defects, thrombocytopenia and hepatic dysfunction. Long-term administration of anti-coagulants can particularly increase risk of life-threatening illness (see e.g., Gilman et al., supra).

Protein-based agents are potentially safer, but generally are limited to treatment of acute conditions and often are restricted to parenteral administration. Such agents are considered less suitable for long-term therapies for chronic diseases (such as atherosclerosis, a major cause of heart attack) due to the increased probability of immune response to a protein therapeutic, relatively high production cost and/or limited oral bioavailability.

It would thus be desirable to have new anti-coagulant agents. It would be particularly desirable to have new anti-coagulant agents that could be administered over a relatively long period to treat chronic conditions such as atherosclerosis.

SUMMARY OF THE INVENTION

We have now discovered pharmaceutically active compounds and compositions that are useful to treat or prevent undesired thrombosis. Preferred compounds of the invention are tissue factor (TF) antagonists that preferably specifically block human factor X and IX activation catalyzed by human tissue factor/factor VIIa complex. Also discovered are methods for treating or preventing thrombosis that use the compounds and compositions disclosed herein.

More particular methods of this invention include administering a therapeutically effective amount of at least one compound or composition of this invention. The compound or composition is typically given to a mammal in need of such treatment such as a human patient who is susceptible to, suffering from, or recovering from undesired thrombosis, or mammal that is suffering from, recovering from or susceptible to other disease or disorder impacted by tissue factor such as a cardiovascular disease, cell proliferation disorder, post-operative complication, or an immune disorder. Preferred compounds and compositions may also be used to treat or prevent recognized disorders impacted by various thromboses such as those particular disorders disclosed herein.

The invention also includes methods for blocking or inhibiting tissue factor-dependent activation of factor X and/or factor IX. These methods in general include contacting tissue factor with a TF blocking compound to thereby inhibit formation of a functional complex of factor X or factor IX with tissue factor or TF/VIIa. Preferably the TF blocking compound binds to tissue factor to thereby inhibit formation of the functional complex. Inhibition or prevention of formation of such a functional complex can have quite broad application, including for treatment of the above-mentioned diseases or disorders in mammals, particularly humans suffering from or susceptible to such diseases or disorders.

Preferred compounds of the invention generally exhibit good blocking activity in at least one test for detecting and preferably measuring TF-mediated blood clotting. More particular tests are standard in vitro assays for measuring activity of a specific blood coagulation factor in which the assay is recognized as providing optimal results in the presence of TF or a TF-associated complex such as the human TF/VIIa complex. The TF can be provided in the assay as a recombinant molecule or molecule purified from natural sources depending usually on the specific assay selected.

A more particular in vitro assay detects and measures activity of a specific blood coagulation factor which has a recognized activity enhanced in the presence of human TF or the human TF/VIIa complex. Of preferred interest are standard in vitro assays for measuring TF-dependent activation of factor X to FXa and factor IX to FIXa. Sometimes these assays will be referred to herein as a "primary screening assay" or related term or phrase such as "method of discovery" to denote preferred use of the assay in screening compounds.

For example, a particularly preferred compound of the invention will exhibit good blocking activity in the primary screening assay for measuring TF-dependent activation of factor X to FXa. Additionally preferred compounds will exhibit good blocking activity in the primary screening assay for measuring TF-dependent activation of factor IX to FIXa.

It will be appreciated that by the phrase "good blocking activity" or related phrase is meant preferred use of a compound of this invention to reduce or inhibit TF/VIIa-dependent activation of factor X to FXa and/or factor IX to FIXa. A preferred compound is a synthetic or semi-synthetic compound such as those small molecule compounds disclosed below. More particular disclosure relating to the primary screening assays is provided as follows.

Preferred compounds of this invention will exhibit an $IC_{50}$ (concentration required to inhibit factor X activation by about 50% relative to a suitable control) of about 100 µM or less and preferably about 10 µM or less. Additionally preferred compounds will exhibit equivalent or greater than about 70% inhibition of TF- or TF/VIIa dependent FX activation in the assay. In a preferred embodiment, the primary screening assay includes all of the following steps:

1) admixing in a suitable assay solution TF/VIIa complex and factor X under conditions conducive to forming factor Xa,
2) contacting the solution with a detectably-labeled factor Xa substrate; and
3) detecting labeled product in the solution as being indicative of the factor X activation.

Preferred use of this primary screening assay effectively measures the capability of a candidate compound to decrease or eliminate TF- or TF/VIIa dependent factor X activation. The assay is generally flexible and can be manipulated as necessary to test a compound for capability to block factor X activation. For example, the candidate compound can be added at any one or more of the steps shown above with addition of the compound at step 1) being preferred for many screening applications.

A preferred TF/VIIa complex for use in the method includes TF which has been exposed to conditions conducive to exposing good TF blocking sites. More specific conditions for isolating and using the TF are provided below.

As mentioned above, another primary screening assay is a standard in vitro assay for measuring factor IX activation by TF or TF/VIIa. In this example, a preferred compound will exhibit an $IC_{50}$ (concentration required to inhibit factor IX activation in the assay by about 50% relative to a suitable control) in the assay of about 200 µM or less, and preferably about 10 µM or less. In a preferred embodiment, the standard assay for measuring the factor IX activation includes all of the following steps:

1) admixing in a suitable assay solution TF/VIIa complex with factor IX under conditions conducive to forming factor FIXa,
2) contacting the solution with FX and detectably-labeled FXa substrate; and
3) detecting labeled product in the solution as being indicative of the factor IXa activation by TF/VIIa.

In preferred embodiments, this screening assay effectively measures capacity or capability of the candidate compound to decrease or eliminate factor IX activation. The assay is generally sensitive to TF- or TF/VIIa-dependent formation of FIXa and can be used in several ways to test a desired compound for capacity or capability to block the factor IX activation. For example, a compound to be further tested can be added at one or more of the steps shown above with addition of the compound at step 1) being preferred for most screening applications. Typically preferred compounds of this invention will exhibit good blocking activity in this example of the primary screening assay.

A further preferred primary screen of the invention is the Prothrombin Time (PT) test or assay which measures extrinsic pathway clotting. This test is standard in the field and is routinely used to measure clotting in biological samples such as blood plasma.

More particularly preferred compounds of this invention will exhibit good inhibitory activity in the PT assay. A typically preferred compound will increase plasma clotting time in the PT assay relative to a suitable control by at least about 5% to about 10% (seconds). Preferred use of the PT assay measures TF-mediated blood plasma clot time and is performed as follows:

1) providing citrated plasma in a suitable assay solution under conditions conducive to plasma coagulation,
2) admixing a suitable tissue factor preparation and calcium in the solution under conditions suitable for initiating plasma clotting; and
3) measuring the clot time in the solution to determine the prothrombin clot time (PT).

Preferred use of the PT assay measures capability of the compound tested to prolong the prothrombin clot time. The PT assay is well known in this field and can be employed in one or a combination of ways to test the compound for capacity or capability to increase or block the prothrombin clot time.

Especially preferred compounds of this invention exhibit good activity in at least one of the primary assays mentioned above (factor X, factor IX activation and/or PT tests).

Good inhibition of the TF- or TF/VIIa-dependent activation in any one or more of the above primary screening assays at least in many cases can be attributed to effects of the compound on TF/VIIa and/or FXa activities. As discussed, preferred compounds of the invention are TF-antagonists and generally exhibit good blocking activity in preferred in vitro assays for measuring TF-mediated blood coagulation. Thus it will usually be desirable to further test compounds giving good blocking activity in one or more of the above primary screening assays and in at least one and preferably more than one of the "secondary screening assays" discussed below. Such secondary assays can facilitate further identification and selection of candidate compounds having desired TF-antagonist activity, e.g., by eliminating from consideration compounds having activity other than desired activity such as compounds impacting protease activity.

A variety of secondary assays can be conducted in accord with this invention to further evaluate compounds identified in a primary assay, e.g. to further evaluate activity identified in a primary assay or to determine the presence of a certain undesired activity. For example, additionally preferred compounds of this invention will exhibit substantially reduced or negligible activity in other secondary screening assays which are not optimized to measure TF-antagonism. That is, these secondary assays may not be TF dependent. Particular examples of such assays include those formatted to measure thrombin, trypsin, or activated factors such as FXa, FIXa, or FVIIa. Also, preferred compounds exhibit negligible activity in an Activated Partial Thromboplastin Time (APTT) test or assay. More specific examples of such secondary screening assays are provided in the discussion and Examples which follow.

In any one or all of the assays disclosed herein including the primary screens and secondary tests discussed above, the candidate compound can be provided in the assay as the sole active agent or it can be combined with other agents to be tested including other compounds or compositions of this invention. In this embodiment, the screening assays are particularly useful for detecting and preferably quantifying synergism between the compounds, agents or compositions.

A variety of inhibitors against human tissue factor are disclosed herein. These compounds can be used in the screening assays described herein as well as the treatment and prevention methods of this invention.

For example, disclosed herein are phosphonate compounds that are sometimes referenced herein as "TF antagonists", "TF blocking compounds" or similar phrase. Preferred compounds of the invention are small molecules and do not include peptide linkage groups. More particular compounds consist of a phosphonate group and a "headpiece". Typically, the headpiece is covalently bound to the phosphonate group and will include or consist of an amine group or a cyclic ring such as an aromatic group. In embodiments in which the headpiece includes the aromatic group, the headpiece will preferably be linked to a phosphonate (preferably bisphosphonate) group by a nitrogen or oxygen atom. Particular aromatic groups are phenyl groups which can be substituted with one or more other groups as discussed below. In embodiments in which the headpiece is an amine group, it will be appreciated that the compound will be representative of a primary or further substituted amine compound.

More specifically, preferred compounds of the invention include those of the following Formula I:

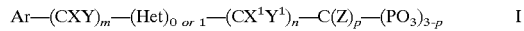

Ar is optionally substituted carbocyclic aryl or optionally substituted heteroaryl;
Het is optionally substituted N, O, S, S(O) or S(O$_2$);
each X, each Y, each X', each Y' and each Z are each independently hydrogen; halogen; hydroxyl; sulfhydryl; amino; optionally substituted alkyl preferably having 1 to about 12 carbons, more preferably 1 to about 6 carbons; optionally substituted alkenyl preferably having from about 2 to 12 carbon atoms, more preferably about 2 to 6 carbons; optionally substituted alkynyl preferably having from about 2 to 12 carbon atoms, more preferably about 2 to 6 carbon atoms; optionally substituted alkoxy preferably having 1 to about 12 carbon atoms, more preferably 1 to about 6 carbon atoms; optionally substituted alkylthio preferably having from about 1 to 12 carbon atoms, more preferably about 1 to 6 carbon atoms; optionally substituted alkylsulfinyl preferably having from about 1 to 12 carbon atoms, more preferably about 1 to 6 carbon atoms; optionally substituted alkylsulfonyl preferably having from about 1 to 12 carbon atoms, more preferably about 1 to 6 carbon atoms; or optionally substituted alkylamino preferably having from about 1 to 12 carbon atoms, more preferably about 1 to 6 carbon atoms;

m is an integer of from 0 (where the hetero atom is directly substituted on the aryl group) to 4, and preferably is 0, 1 or 2;

n is an integer of from 0 to 4, and preferably n is 1 or 2;

p is 1 (where the compound is a bisphosphonate) or 2 (where the compound has a single terminal PO$_3$ group);

and pharmaceutically acceptable salts thereof.

It is understood that in Formula I above, and elsewhere the designation of "(Het)$_{0\ or\ 1}$" specifies that the Het group may be absent (i.e. where the Het subscript is zero) or present in a single occurrence (i.e. where the Het subscript is one).

Additional preferred compounds include those of the above formula where Ar is a carbocyclic aryl group, particularly phenyl, such as compounds of the following Formula II:

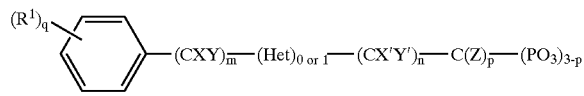

wherein X, Y, Het, X', Y', Z, m, n, and p are the same as defined in Formula I above;

wherein each R$^1$ is independently halogen (F, Cl, Br, I); amino; hydroxy; nitro; carboxy; sulfhydryl; optionally substituted alkyl preferably having 1 to about 20 carbon atoms, more preferably 1 to about 10 carbon atoms, still more preferably 1 to about 6 carbon atoms; optionally substituted alkenyl preferably having 2 to about 20 carbon atoms, more preferably 2 to about 10 carbon atoms, still more preferably 2 to about 6 carbon atoms; optionally substituted alkynyl preferably having 2 to about 20 carbon atoms, more preferably 2 to about 10 carbon atoms, still more preferably 2 to about 6 carbon atoms; optionally substituted alkoxy preferably having 1 to about 20 carbon atoms, more preferably 1 to about 10 carbon atoms, still more preferably 1 to about 6 carbon atoms; optionally substituted alkylthio preferably having 1 to about 20 carbon atoms, more preferably 1 to about 10 carbon atoms, still more preferably 1 to about 6 carbon atoms; optionally substituted alkylsulfinyl preferably having 1 to about 20 carbon atoms, more preferably 1 to about 10 carbon atoms, still more preferably 1 to about 6 carbon atoms; optionally substituted alkylsulfonyl preferably having 1 to about 20 carbon atoms, more preferably 1 to about 10 carbon atoms, still more preferably 1 to about 6 carbon atoms; optionally substituted alkylamino preferably having 1 to about 20 carbon atoms, more preferably 1 to about 10 carbon atoms, still more preferably 1 to about 6 carbon atoms; optionally substituted alkanoyl preferably having 1 to about 20 carbon atoms, more preferably 1 to about 10 carbon atoms, still more preferably 1 to about 6 carbon atoms; optionally substituted carbocyclic aryl; or optionally substituted aralkyl;

q is an integer of from 0 (where the phenyl ring positions are fully hydrogen substituted) to 5, and preferably m is 0, 1 2 or 3; and pharmaceutically acceptable salts thereof.

Of the compounds of the above Formulae I and II, additional compounds include those where the group Het is optionally substituted nitrogen or oxygen, such as compounds of the following Formulae III and IV:

III

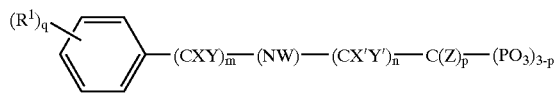

IV

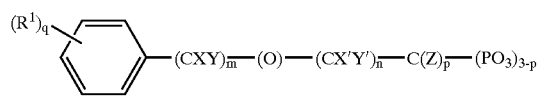

wherein in each of Formula III and IV, $R^1$, X, Y, X', Y', Z, q, m, n, and p are the same as defined in Formulae I and II above; and W is hydrogen, optionally substituted alkyl, preferably having 1 to about 8 carbon atoms, more preferably 1 to about 6 carbon atoms; optionally substituted alkenyl, preferably having 2 to about 8 carbon atoms, more preferably 2 to about 6 carbon atoms; optionally substituted alkynyl, preferably having 2 to about 8 carbon atoms, more preferably 2 to about 6 carbon atoms; optionally substituted alkoxy, preferably having 1 to about 8 carbon atoms, more preferably 1 to about 6 carbon atoms; optionally substituted alkylthio, preferably having 1 to about 8 carbon atoms, more preferably 1 to about 6 carbon atoms; optionally substituted alkylsulfinyl, preferably having 1 to about 8 carbon atoms, more preferably 1 to about 6 carbon atoms; optionally substituted alkylsulfonyl; optionally substituted alkylamino; optionally substituted alkanoyl, preferably having 1 to about 8 carbon atoms, more preferably 1 to about 6 carbon atoms; optionally substituted carbocyclic aryl; or optionally substituted aralkyl; and pharmaceutically acceptable salts thereof Additional compounds of Formula III include those where the nitrogen group is a direct (no interposed carbon or other atoms) phenyl ring substituent, and particularly preferred compounds of Formula IV include those where the oxygen is a direct ring substituent or a single methylene group is present, such as compounds of the following Formulae IIIa and IVa:

IIIa

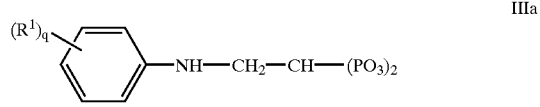

IVa

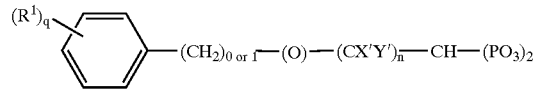

wherein $R^1$, X', Y', n and q are the same as defined in Formulae I and II above; and pharmaceutically acceptable salts of those compounds.

Additional compounds of the invention bind tissue factor (TF) so that FX does not effectively bind to the TF/factor VIIa complex whereby FX is not effectively converted to its activated form (FXa). Preferred compounds of the invention can inhibit TF function by effectively blocking FX binding or access to TF molecules. See, for instance, the results of Example 2 which follows. As used herein, references herein to "compounds of the invention" are inclusive of compounds of Formulae I, II, III, IIA, IV and IVA above.

In preferred aspects, the invention provides methods for inhibiting blood coagulation and blood clot formation in a mammal, methods for inhibiting thrombin generation in a mammal, and methods for treating or preventing thromboembolic disorders in a mammal. The methods of the invention in general comprise administering to a mammal, such as a primate particularly a human, a therapeutically effective amount of a compound of the invention.

Compounds of the invention are particularly useful to alleviate various diseases impacted by tissue factor (TF). By the term "impacted" is meant that the severity or duration of the disease is increased by presence of the TF according to the recognized assays or tests. Particular diseases include thromboses, especially to prevent or inhibit restenosis, or other thromboses following an invasive medical procedure such as arterial or cardiac surgery (e.g., angioplasty or endartectomy), including for prophylaxis of deep vein thrombosis associated with orthopedic or other surgery. Compounds of the invention also can be employed to reduce or even effectively eliminate blood coagulation arising from use of medical implementation (e.g., a catheter, stent, arteriovenous shunt or other medical device). Compounds of the invention also will be useful for prophylaxis for long term risk for myocardial infarction. Compounds of the invention also will be useful for treatment of thrombotic conditions that may be associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis.

Additional uses for the present compounds include use in the treatment of atherosclerosis, inflammation, and as an anti-angiogenic agent, especially to treat cancers, particularly solid cancers such as cancers residing in the lung, breast, liver, brain or other tissue.

Compounds of the invention also can be employed as an anti-coagulant in extracorporeal circulation of a mammal, particularly a human subject. In such methods, one or more compounds of the invention is administered to the mammal in an amount sufficient to inhibit blood coagulation prior to or during extracorporeal circulation such as may be occur with cardiopulmonary bypass surgery, organ transplant surgery or other prolonged surgeries.

Compounds of the invention also can be employed in in vivo diagnostic methods including in vivo diagnostic imaging of a patient.

Compounds of the invention also can be used in in vitro assays, e.g. to selectively inhibit factor X activation. Such assays of the invention will be useful to determine the presence or likelihood of a patient having blood coagulation or a blood clot.

Pharmaceutical compositions also are provided comprising an effective amount of one or more compounds of the invention and a pharmaceutically acceptable carrier.

Other aspects of the invention are discussed infra.

BREIF DESCRIPTION OF THE DRAWINGS

FIG. 1 is a flow chart of a screening assay employed in examples below.

FIGS. 2(a), 2(b), 2(c) and 2(d) disclose results of examples which follow.

FIG. 3 is a table showing $IC_{50}$ values and inhibition of protease activities by certain TF antagonists of this invention, i.e. compounds 1, 2, 3, 4, and 6. The compound labeled "Fosamax" is represented by the formula $NH_2$-bisphosphonate.

FIG. 4 is a table showing the effect of specific TF antagonists (compounds 1 and 2) in the prothrombin time (PT) assay.

FIG. 5 is a table showing effects of compound 1 on Km values for FX in TF/VIIa-dependent activation assay.

DETAILED DESCRIPTION OF THE INVENTION

Figure 1:
Figure 1:
Figure 1:
Figure 1:
Figure 1:

As discussed, the present invention features compounds such as pharmaceutically active compounds and especially pharmaceutical compositions that utilize or comprise one or more of such compounds. Preferred compounds are effective TF antagonists as determined by standard in vitro screening assays disclosed herein. Especially preferred compounds are very useful for the treatment or prophylaxis of undesired thrombosis. The invention has a wide spectrum of applications including use in screening candidate compounds having significant TF-antagonistic activity.

As discussed, preferred compounds and compositions of this invention are good TF antagonists that exhibit significant blocking activity in at least one of and preferably all of the primary screening assays (TF- or TF/VIIa-dependent activation of factor X or factor IX, and PT assay). Especially preferred compounds do not exhibit significant blocking activity in the Activated Partial Thromboplastin Time (APTT) assay discussed previously. Further preferred are those compounds of this invention showing insignificant activity in other secondary assays such as those for measuring trypsin, thrombin, factor Xa, factor IXa, and factor VIIa activity as discussed below.

The standard in vitro assays disclosed herein are well-known in the field and are generally flexible. Moreover, the assays can be conveniently manipulated to detect and quantify TF-antagonistic activity as needed. The assays are typically compatible with testing compounds or compositions of this invention in the presence of other therapeutic or experimental agents giving good anti-platelet, anti-thrombolytic, or anti-coagulant activity. In addition, the assays can be used to test effects with recognized anti-TF antibodies. In these embodiments, the standard in vitro assays are especially useful for detecting and preferably measuring significant co-operative or synergistic effects exhibited by the compounds or compositions of this invention.

A more particular example of the primary screening assay discussed previously is as follows. The assay is standard for measuring TF/VIIa-dependent factor X activation. A preferred compound exhibits an $IC_{50}$ in the assay of less than about 100 μM and preferably less than about 10 μM exemplifying good blocking activity in this assay. In a more preferred embodiment, the primary screening preferably includes the following steps.

1) admixing in a suitable assay solution about 0.1 nM of human recombinant TF/VIIa complex (lipidated), about 180 nM human FX, and between from about 0.5 μl to about 10 μl of at least one compound to be tested (optionally dissolved in an appropriate vehicle such as water or dimethylsulfoxide (DMSO)) and incubating the reaction at 37° C. for a few minutes up to about an hour or more, 2) contacting the solution with a suitable chelating agent such as ethylenediaminetetra acetic acid (EDTA) to reduce or stop factor X activation, 3) contacting the solution with a detectable amount of a chromogenic substrate specific for FXa (e.g., Spectrozyme FXa or S-2765) and incubating same at 37° C.; and 4) detecting chromophore produced in the solution as being indicative of the factor X activation.

Reference herein to a "standard assay for measuring TF/VIIa-dependent factor X activation" or similar phrase will preferably refer to the above steps 1)–4). More specific disclosure relating to the assay can be found in Example 2 below in which the standard assay for measuring TF/VIIa-dependent factor X activation is specifically adapted for spectrophotometric detection of FXa produced chromophores at 405 nm.

A preferred TF/VIIa complex for use in the method includes TF that has been exposed to conditions suitable for exhibiting good TF blocking sites. Such TF molecules can be obtained by one or a combination of approaches. In one method, human TF is obtained from an overproducing immortalized cell line or an acetone powder derived from human brain. TF is preferably isolated in the presence of at least one non-ionic detergent such as TRITON® X-100 (polyoxyethylene (10) isooctylphenyl ether) under moderate conditions of salt and pH, e.g., 100 mM NaCl and pH 8.0. Preferred amounts of the non-ionic detergent will vary depending on intended use but will generally be in an amount of from between about 0.05% to about 0.5% (w/v). See the General Comments of the examples below for more specific information about isolating human TF.

Additionally preferred TF is exposed to conditions in the standard assay for measuring TF/VIIa-dependent factor X activation. See Example 2 below for more specific disclosure about that standard assay.

Additionally preferred compounds of this invention exhibit good blocking activity in the other primary screening assay for measuring TF/VIIa-dependent factor IX activation. Preferred compounds exhibit an $IC_{50}$ in the assay of less than about 200 μM with preferably less than about 10 μM exemplifying good blocking activity in this assay. In a more particular embodiment, the standard assay preferably includes the following steps:

1) admixing in a suitable assay solution about 0.7 nM TF/VIIa complex with 300 nM factor IX and 1000 nM factor X, and from between about 0.5 μl to about 10 μl of at least one compound to be tested (optionally dissolved in an appropriate vehicle such as water or dimethylsulfoxide (DMSO)) and incubating the solution at 37° C. from between about a few minutes up to about an hour under conditions suitable for forming FIXa and FXa;

2) contacting the solution with a suitable chelating agent such as EDTA to stop FIX activation;

3) contacting the solution with a chromogenic substrate specific for the FXa (e.g., Spectrozyme FXa) and incubating same at 37° C.; and 4) detecting chromophore in the solution as being indicative of the factor IX activation.

Reference herein to a "standard assay for measuring TF/VIIa dependent factor IX activation" or similar term or phrase will specifically refer to the above steps 1)–4). See Example 2 below for a more specific illustration of the standard assay adapted for spectrophotometric detection of preferred chromophore at 405 nm.

The table in FIG. 3 below shows specific $IC_{50}$ values for specific TF antagonists of the invention, i.e. compound 1, compound 2, compound 3, compound 4, and compound 6, as well as Fosamax. The values were determined in the standard assays for measuring TF/VIIa-dependent factor X activation and TF/VIIa-dependent factor IX activation. As can be seen from the table in FIG. 3, these compounds give good blocking activity in these assays.

As discussed, additionally preferred compounds of this invention exhibit good clot time inhibition in the PT assay, preferably an increase in clotting time from between about 20% to at least 100%, and more preferably from between about 20% to at least 500% relative to a suitable control. Clot times are generally measured in seconds. Preferred PT assays are typically performed by adding a suitable amount (e.g. about 1 to 3 nM) of lipidated tissue factor to an assay solution that includes conventionally citrated plasma. The PT assay measures TF-mediated blood plasma clot time and is preferably performed by conducting the following steps:

1) providing about 0.1 ml of citrated human plasma in a suitable assay solution, and combining same with between from about 0.5 µl to 10 µl of at least one compound to be tested (optionally dissolved in vehicle such as water or dimethylsulfoxide (DMSO)) and incubating same at room temperature for about 3 to 10 minutes, 2) admixing into the solution from between about 0.2 ml (ca. 1–3 nM recombinant human tissue factor) and about 5–10 mM of calcium to initiate plasma clotting; and 3) measuring the plasma clot time to determine the prothrombin clot time (PT).

Reference herein to a "standard PT assay" or similar phrase or term will specifically refer to the above steps 1)–3). See also *Williams Hematology*, 5$^{th}$ Ed. (Beutler, E. et al. Eds.) McGraw-Hill, Inc. Health Professions Div., New York, for more specific disclosure relating to conducting the PT assay.

As mentioned, the present invention provides a variety of assays for detecting and preferably measuring capability of preferred compounds of this invention to antagonize good TF activity. As has also been discussed, certain standard in vitro screening assays are sometimes referred to herein as "secondary screening assays" to denote preferred use with one or more or all of the primary screening assays mentioned previously. Practice of such particular secondary screening assays in conjunction with one or more of the primary screening assays will provide a wide spectrum of useful compounds featuring good anti-TF activity.

Secondary screening assays are disclosed herein and include those optimized to detect and preferably measure the catalytic activities of factor VIIa (FVIIa), factor IXa (FIXa), factor Xa (FXa), thrombin, trypsin, or Russell's viper venom (RVV). In most instances, optimal practice of these assays does not require added TF. Preferred compounds of this invention are specific TF-antagonists and will generally exhibit substantially reduced or negligible activity in these assays. Practice of the secondary screening tests in conjunction with the primary and preferred secondary screening assays discussed previously will facilitate selection of preferred compounds exhibiting highly specific anti-TF activity. Reference herein to "reduced" or "negligible" activity with respect to these secondary screening assays is meant to denote between from about 2% to about 10% of the activity exhibited by a suitable control such as water or DMSO.

As discussed above, the invention provides a wide spectrum of pharmaceutically active compounds and compositions that are useful to treat or prevent undesired thrombosis. Preferred compounds are tissue factor (TF) antagonists and preferably can specifically block human factor X and IX activation catalyzed by human tissue factor/factor VIIa complex. Illustrative compounds of the invention include the anti-coagulant phosphonate of the above-defined Formula I, II, III, IIIA, IV, and IVA.

Illustrative compounds of the invention are bisphosphonate, i.e. compounds of the above formulae where p is 1 and two —PO$_3$ groups are present. Preferred R$^1$ ring substituents of the above formulae include hydroxy, halogen, alkyl such as $C_{1-6}$ alkyl, amino, and alkylamino such as mono-or di-($C_{1-4}$)alkyl. Preferred W groups (optional amino substituent) include hydrogen, and optionally substituted alkyl, particularly $C_{1-6}$ optionally substituted alky. Preferred X, Y, X', Y' and Z groups include hydrogen and optionally substituted alkyl, particularly $C_{1-6}$ optionally substituted alkyl.

Additional compounds of the invention include the following compounds 1 through 6, and pharmaceutically acceptable salts of those compounds. Compounds 1, 2 and 6 below are particularly preferred. Those compound designations 1 through 6 are used throughout the present disclosure and refer to the specified compounds of the structures shown immediately below.

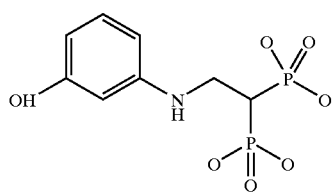

1

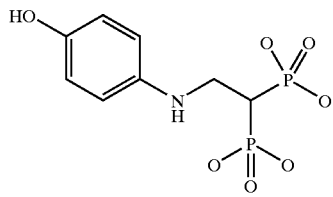

2

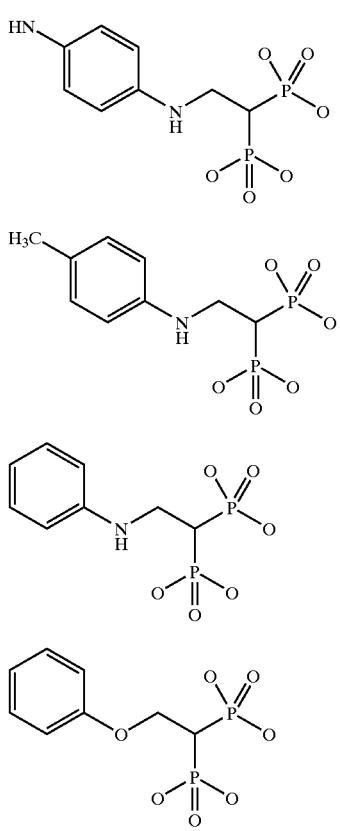

Suitable halogen substituent groups of compounds of the invention (which includes e.g. compounds of Formulae I, II, III, IIIA, IV and/or IVA as those formulae are defined above) are F, Cl, Br and I. As used herein, the term alkyl unless otherwise modified refers to both cyclic and noncyclic groups, although cyclic groups will comprise at least three carbon ring atoms. Alicyclic alkyl groups are generally preferred. Alkenyl and alkynyl groups of compounds of the invention have one or more unsaturated linkages, typically 1 to about 3 or 4 unsaturated linkages. Also, the terms alkenyl and alkynyl as used herein refer to both cyclic and noncyclic groups, although straight or branched noncyclic groups are generally more preferred. Alkoxy groups of compounds of the invention have one or more oxygen linkages, typically 1 to about 5 or 6 oxygen linkages. Alkylthio groups of compounds of the invention have one or more thioether linkages, typically 1 to about 5 or 6 thioether linkages. Alkylsulfinyl groups of compound of the invention have one or more sulfinyl (SO) linkages, typically 1 to about 5 or 6 sulfinyl linkages. Alkylsulfonyl groups of compounds of the invention have one or more sulfonyl ($SO_2$) linkages, typically 1 to about 5 or 6 sulfonyl linkages. Preferred alkylamino groups of compounds of the invention include those groups having one or more primary, secondary and/or tertiary amine groups, preferably 1 to about 3 or 4 amine groups. Suitable alkanoyl groups have one or more carbonyl groups, typically 1 to about 4 or 5 carbonyl groups. Alkoxy, alkylthio, alkylsulfinyl, alkylsulfonyl, alkanoyl and other groups may be suitably either linear or branched. Carbocyclic aryl as used herein refers to non-hetero aromatic groups that have 1 to 3 separate or fused rings and 6 to about 18 carbon ring members and may include e.g. phenyl, naphthyl, biphenyl, acenaphthyl, phenanthracyl, and the like. Phenyl and naphthyl are often preferred. Suitable heteroaromatic or heteroaryl groups will have 1 to 3 rings, 3 to 8 ring members in each ring and from 1 to about 3 hetero atoms (N, O or S). Specifically suitable heteroaromatic or heteroaryl groups include e.g. courmarinyl, quinolinyl, pyridyl, pyrazinyl, pyrimdinyl, furyl, pyrrolyl, thienyl, thiazolyl, oxazolyl, imidazolyl, indolyl, benzofuranyl, and benzothiazol.

Compounds of Formulae II, III, IIIA, IV and/or IVA as those formulae are defined above preferably have a $R^1$ group present as a para substituent on the phenyl ring.

As discussed above, R', W, X, Y, X', Y', nitrogen "Het" groups, and Z groups are optionally substituted. Suitable groups that may be present on a "substituted" R', W, X, Y, X', Y', Het and Z substituent include e.g. halogen such as fluoro, chloro, bromo and iodo; cyano; hydroxyl; nitro; azido; sulfhydryl; alkanoyl e.g. $C_{1-6}$ alkanoyl group such as acetyl and the like; carboxamido; alkyl groups including those groups having 1 to about 12 carbon atoms, preferably from 1 to about 6 carbon atoms; alkenyl and alkynyl groups including groups having one or more unsaturated linkages and from 2 to about 12 carbon atoms, preferably from 2 to about 6 carbon atoms; alkoxy groups having one or more oxygen linkages and from 1 to about 12 carbon atoms, preferably 1 to about 6 carbon atoms; aryloxy such as phenoxy; alkylthio groups including those moieties having one or more thioether linkages and from 1 to about 12 carbon atoms, preferably from 1 to about 6 carbon atoms; alkylsulfinyl groups including those moieties having one or more sulfinyl linkages and from 1 to about 12 carbon atoms, preferably from 1 to about 6 carbon atoms; alkylsulfonyl groups including those moieties having one or more sulfonyl linkages and from 1 to about 12 carbon atoms, preferably from 1 to about 6 carbon atoms; aminoalkyl groups such as groups having one or more N atoms and from 1 to about 12 carbon atoms, preferably from 1 to about 6 carbon atoms; carbocyclic aryl having 6 or more carbons, particularly phenyl; aryloxy such as phenoxy; aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl. A "substituted" R', W, X, Y and Z substituent of a compound of the invention may be substituted at one or more available positions, typically 1, 2 or 3 positions, by one or more suitable groups such as those listed immediately above.

Compounds of the invention can be prepared by procedures generally known in the art. For example, phosphonate acids of Formula I can be prepared by formation of the corresponding alkyl diester followed by conversion to the diacid, e.g. by treatment of the diester with bromotrimethylsilane, and then further reaction of that intermediate to provide a compound of the invention. See, for instance, C. R. Degenhardt et al., *J. Org. Chem.*, 51:3488–3490 (1986); I. S. Alfer et al., *Izv. Akad. Nauk SSSR*, 1122–1126 (1984); I. S. Alfer et al., *Izv. Akad. Nauk SSSR*, 2802–2806 (1983); and U.S. Pat. No. 5,728,650. See also Example 1 which follows.

Reference herein to a "TF blocking compound," "TF antagonist" or related term generally includes those compounds disclosed herein exhibiting good blocking activity in at least one of the primary screening assays such as the PT assay. More particular TF blocking compounds specifically bind TF. Without wishing to be bound to theory, the compounds are believed to block FX or FIX from binding TF in a way sufficient to reduce or block activation to FX or FIX, respectively.

Reference to a "therapeutically effective amount" of a composition is such as to produce a desired effect in a host such as a mammal and especially a primate such as a human patient. Preferably the effect can be monitored using several end-points known to those of skill in the field. For example, one desired effect is an increase or stabilization of cardiovascular function as measured, e.g., by enhanced heart function and especially blood flow within subject vessels. Such impact can be monitored and usually measured in terms of a therapeutic effect, e.g., improved cardiovascular function, alleviation of one or more symptoms indicative of compromised heart function or function of related vasculature, or other particularized physiological assays. These specific methods are not intended to be inclusive and further methods intended to suit a specific application such as thrombosis, cancer, or atherosclerosis will be apparent to the skilled worker in the field.

As discussed above, a compound of the invention can be administered to a mammal, preferably a primate such as a human, to prevent or reduce thromboses. Therapies in which compounds of the invention will be useful include treatment or prophylaxis of venous thrombosis and pulmonary embolism, arterial thrombosis e.g. myocardial ischemia, myocardial infarction, unstable angina, stroke associated with thrombosis, and peripheral arterial thrombosis. Compounds of the invention also may be useful for treatment or prophylaxis of atherosclerotic diseases e.g. coronary arterial disease, cerebral arterial disease and peripheral arterial disease. See e.g., Wilde, R. G. et al. *Bioinorganic & Medicinal Chemistry Letters* 167–172 (1995). Compounds of the invention also will be useful for anticoagulation treatment involving artificial organs, cardiac valves, medical implementation (e.g. an indwelling device such as a catheter, stent, etc.) and the like. Compounds of the invention also will be useful for therapy in other disorders or diseases where blood coagulation may be involved as a related disorder, e.g. cancer, inflammatory diseases particularly arthritis, and diabetes.

One or more compounds also may be administered as the sole therapeutic agent(s) in a particular protocol, or the compound(s) of the invention may be administered together with other therapeutic agents, e.g. a pharmaceutical targeted for interaction in the blood clotting mechanism such as streptokinase, tPA, urokinase and other agents that lyse clots. A compound of the invention also can be administered with other agents such as one or more other anti-coagulants (e.g., heparin, hirudin, or hirulog), or an anti-platelet (e.g., ReoPro or aspirin). In such combination therapy, a compound of the invention may be administered prior to, or after administration of one or more other suitable anti-coagulant, anti-platelet, thrombolytic or other agents to boost or prolong desired anti-coagulation activity.

Compounds of this invention can be administered intranasally, orally or by injection, e.g., intramuscular, intraperitoneal, subcutaneous or intravenous injection, or by transdermal, intraocular or enteral means. Intravenous or parenteral administration includes e.g. sub-cutaneous, intraperitoneal or intramuscular administration. Generally preferred is oral administration. The optimal dose can be determined by conventional means. Compounds of the present invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof.

Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

See, in general, *Remington's Pharmaceutical Sciences*, (Mack Publishing Co., Easton Pa., (1980)), for a discussion of suitable administration formulations.

It will be appreciated that the actual preferred amounts of active compounds used in a given therapy will vary according to the specific compound being utilized, the particular compositions formulated, the mode of application, the particular site of administration, etc. Optimal administration for a given protocol of administration can be readily ascertained by those skilled in the art using conventional dosage determination tests conducted with regard to the foregoing guidelines. In general, a suitable effective dose of one or more compounds of Formula I will be in the range of about 0.01 to 100 milligrams per kilogram of bodyweight of recipient per day, preferably in the range of from about 0.01 to 20 to 50 milligrams per kilogram or bodyweight of recipient per day.

All documents mentioned herein are fully incorporated by reference in their entirety.

The following non-limiting examples are illustrative of the invention.

General Comments

In the examples below, purified human factors VIIa, IX and X, thrombin, and Russell's viper venom were obtained from Enzyme Research Laboratories Inc. Trypsin was from Boehriger Mannheim. Chromogenic substrates S-2222, S-2288, S-2238, and S-2765 were from DiaPharma Group Inc., and Spectrozyme FXa was from American Diagnostica Inc. Truncated recombinant human tissue factor (e.g. composed of 243 amino acids) is expressed in *E. coli* and purified by immunoaffinity chromatography. A preferred truncated recombinant human tissue factor lacks the cytoplasmic domain. Native human TF was extracted from human carcinoma cell line J82 with 50 mM Tris-HCl, pH 8.0, containing 0.1 M NaCl, 1 mM EDTA, 0.3% Triton X-100. Native TF from other sources is extracted with the same buffer from animal brain acetone powders. All other reagents were from Sigma.

EXAMPLE 1

Preparation of 1-(bisphosponate)-2-amino(3-hydroxyphenyl)ethyl (Compound 1 Above)

The method of Degenhardt et al., *J. Org. Chem.,* 51: 3488–3490 (1986) can be followed to produce the compound. Briefly, paraformaldehyde (104.2 g, 3.47 mol) and di-ethylamine (50.8 g, 0.69 mol) are combined in 2 liters of methanol and the mixture warmed until clear. The heat is removed and $CH_2(PO_3(CH_2CH_3)_2)_2$ (200 g, 0.69 mol) is added. The mixture is refluxed for 24 hours, and then an additional 2 liters of methanol is added, and the solution concentrated under reduced pressure at 35° C. 1 liter of toluene is added to the concentrate, and the resulting solution concentrated, and the toluene addition and concentration repeated. The resulting intermediate is then dissolved in 1 liter of dry toluene, p-toluenesulfonic acid monohydrate (0.50 g) is added and the mixture is refluxed. Resulting methanol is removed, e.g. via a Dean-Stark trap or molecular sieves. After 14 hours the solution can be concentrated, diluted in chloroform, washed with water (2×150 ml), dried over $MgSO_4$ and concentrated, The resulting compound, $CH_2=C(PO_3(CH_2CH_3)_2)_2$, can be purified if desired such as distillation. The compound $CH_2=C(PO_3(CH_2CH_3)_2)_2$ can then be reacted as desired to provide compounds of the invention. In particular, to provide the title compound, $CH_2=C(PO_3(CH_2CH_3)_2)_2$, can be reacted with $NH_2$(3-hydroxyphenyl) in a Michael reaction. The phosphono di-ester can be converted to the di-acid by treatment with bromotrimethylsilane (see, e.g. Morita et al., *Bull. Chem. Soc. Jpn.,* 54:267 (1981)).

EXAMPLE 2

Screening

The primary screening for compounds that inhibit tissue factor/factor VIIa (TF/VIIa) is based on TF/VIIa-dependent FX activation assay (See flow chart in FIG. 1 of the drawings). In this assay, the ability of TF/VIIa complex to activate FX is determined in two discontinuous stages. In the first stage (FX activation), the inactive FX is converted to an active enzyme form, FXa, by TF/VIIa in the presence of phospholipids and calcium. In the second stage (FXa activity assay), EDTA is added at indicated times to the FX activation mixture to chelate calcium, thus leading to the termination of FX→FXa conversion. Calcium is required for TF/VIIa activity. The activity of FXa is then measured by FXa-specific chromogenic substrates such as S-2222, S-2765, or Spectrozyme FXa. In the primary screening, compounds from a previously prepared chemical library are first tested at relatively high concentrations (~0.833 mM) in TF/VIIa-dependent FX activation assay to identify hits of potential TF pathway antagonists (see FIG. 1). However, it is evident that the inhibition of TF/VIIa-dependent FX activation by a compound in this enzyme-coupled assay can be attributed to effects of the compound on TF/VIIa and/or FXa activities. Thus, secondary screening tests are designed to determine how inhibition takes place and the inhibition mechanism. In secondary screening experiments, effects of those compounds identified from primary screening are tested on catalytic activities of factor VIIa (FVIIa), factor IXa (FIXa), factor Xa (FXa), thrombin, Russell's viper venom (RVV), and trypsin. Additional tests such as the TF/VIIa-dependent factor IX activation assay and the prothrombin time (PT) assay were conducted to confirm desired activity, and secondary tests were conducted to further select compounds with good TF-antagonistic activity and that did not exhibit undesired activity.

A. Primary Screening: TF/VIIa-dependent FX Activation

Primary screening was done in duplicate in 96-well plates using the TF/VIIa-dependent FX activation assay. All compounds to be screened were dissolved in dimethyl sulfoxide (DMSO), other reagents were prepared or diluted in 25 mM HEPES-NaOH, 5 mM $CaCl_2$, 150 mM NaCl, 0.1% BSA, pH 7.5. For assays where TF was used, purified human recombinant TF (100 nM) was first lipidated with phosphatidylcholine (0.07 mg/ml) and phosphatidylserine (0.03 mg/ml) in 50 mM Tris-HCl, pH 7.5, 0.1% bovine serum albumin (BSA) for 30 minutes at 37° C. A stock solution of TF/VIIa complex was then prepared by combining equal volumes of 100 nM lipidated TF and 100 nM FVIIa. The complex was incubated at 37° C. for 30 minutes and then was aliquoted and stored at −70° C. for future uses.

For screening assays, 5 µl of each compound (about 10 mM in DMSO) or DMSO were placed in each well of a 96-well plate, followed by adding 45 µl of TF/VIIa complex (0.1 nM). The components in each well were mixed either with pipette tips or by shaking the plate on a Lab-Line titer plate shaker for 30 seconds. After 15 minutes incubation of the plate at a 37° C., 10 µl of human FX (180 nM) was added to each well and mixed as above. The plate was then incubated at 37° C. for 3 to 15 minutes, followed by addition of 10 µl of EDTA (400 mM in 144 mM HEPES, 864 mM NaCl, 0.576% BSA, pH adjusted to 7.5) to each well to terminate FX activation. Ten microliters of FXa substrate (5 mM Spectrozyme FXa, or 3.2 mM S-2765) was added to each well to measure FXa activity. The plate was mixed as above, and after about a 15 minute incubation at 37° C., FXa activity was quenched with 20 µl of 50% acetic acid. Absorbance at 405 nm was then read by an ELISA reader. The $OD_{405nm}$ values were transferred to a Microsoft Excel file and the percent inhibition of TF/VIIa-dependent FX activation was calculated by the following formula:

$$\% \text{ Inhibition}=100-(100 \times A/B)$$

where A and B are the OD values in the presence and absence of a compound, respectively. Any compound showing equivalent or greater than 70% inhibition of TF/VIIa-dependent FX activation was designated as a candidate for secondary screening test.

B. Secondary Screening

Those compounds identified in primary screening were retested in TF/VIIa-dependent FX activation assay at 10-, 50- or 100-fold diluted concentrations (see flow chart of FIG. 1 of the drawings). Compounds that failed to show significant inhibition at diluted concentrations, indicating that the inhibition is either non-specific or very weak, were not tested further. Compounds that inhibited TF/VIIa-dependent FX activation at diluted concentrations were further tested for their ability to inhibit activities of the following proteases, trypsin, RVV, thrombin, FXa, FVIIa, and FIXa. A target was to identify compounds that specifically prevent FX (and FIX) binding to TF/VIIa complex or interfere with TF and VIIa interaction so that FX (and FIX) activation is blocked. However, those compounds that have broad ability (non-specific) to inhibit several protease activities were not further investigated. Compounds that met the specified criteria, that is, to inhibit TF/VIIa-dependent FX activation at lower concentrations (<0.1 mM) but without significant effects on protease activities, were selected, including compounds 1 and 2, whose structures are shown above, identified as strong TF antagonists and investigated further.

EXAMPLE 3

Effects of Compounds of the Invention on FVIIa, FXa, Thrombin, and Trypsin

To test whether compounds 1 and 2 inhibit coagulation proteases and trypsin, the following assays were conducted.

A. FVIIa Activity Assay

Factor VIIa (FVIIa) activity, or the effect of TF and FVIIa interactions, can be determined in the presence of TF using FX and a small peptide (chromogenic) substrate or in the absence of TF using FX as substrate. Assays using FVIIa-specific chromogenic substrate S-2288 directly measures the effect of a compound on FVIIa catalytic activity. In this assay, 55 µl of TF/FVIIa complex (containing 10 nM TF and 10 nM VIIa) was first incubated with 5 µl of DMSO (or diluted DMSO) or compound, in a 96-well plate for 15 minutes at 37° C., then admixed with 20 µl of 8 mM S-2288. The reaction was incubated for 1–2 hours at 37° C. Absorbance at 405 nm was then measured after the reaction was quenched with 20 µl of 50% acetic acid. The percent inhibition of TF/VIIa activity was calculated from $OD_{405nm}$ values in the absence and presence of a compound. Results are shown in Table 1 (FIG. 2($a$)) and show that compounds 1 and 2 do not have significant effect on TF/VIIa catalytic activity toward S-2288, indicating that these compounds do not bind to the active site of FVIIa, nor do they interfere with TF and VIIa interactions. Inhibition of TF/VIIa activity toward S-2288 by the two compounds would be expected if they were to bind to VIIa active site or prevent TF and VIIa from forming an active complex.

B. FXa Activity Assay

FX is converted to FXa by TF/VIIa complex in the absence of any compound. To do that, 54 µl of TF/VIIa (50 nM) was added to 27 ml of buffer in a 50-ml tube. Then 6 ml of FX (180 nM) was added and incubated at 37° C. for 15 minutes. Six ml of EDTA was added to stop FX activation. Five µl of compound or DMSO was placed in each well of a 96-well plate in duplicate, then 65 µl of FXa generated above was added to each well and mixed. After incubation for 15 minutes at 37° C., 10 µl of FXa substrate Spectrozyme FXa was added and incubated for 20 minutes at 37° C. Absorbance at 405 nm was then measured following addition of 20 µl of 50% acetic acid. The percent inhibition of FXa activity was calculated from $OD_{405nm}$ values in the absence and presence of a compound. Results shown in Table 1 (FIG. 2($a$)) indicate that compounds 1 and 2 do not inhibit FXa activity, suggesting that inhibition of TF/VIIa-dependent FX activation is not due to the inhibition of FXa activity by these two compounds.

C. Thrombin Activity Assay

For thrombin activity assay, 55 µl of buffer was mixed with 5 µl of DMSO or compound, followed by addition of 10 µl of thrombin (20 nM). Mix and incubate at 37° C. for 10 minutes. Then 10 µl of substrate S-2238 was added and allowed to incubate at 37° C. for 15–20 minutes. Absorbance at 405 nm was then measured and the percent inhibition of thrombin activity was calculated from $OD_{405nm}$, values in the absence and presence of a compound. Results shown Table 1 (FIG. 2($a$)) indicated that compounds 1 and 2 (structures shown above) do not inhibit thrombin activity.

D. Trypsin Activity

For trypsin activity assay, 4 µl of trypsin (100 nM) was first mixed with 61 µl of buffer, 5 µl of DMSO or 5 µl of compound (in DMSO), followed by 15 minute incubation at 37° C. Then 10 µl of substrate S-2222 (4.8 mM) was added to start the reaction. After a 15 minute incubation at 37° C., 20 µl of 50% acetic acid was added to quench the reaction. Absorbance at 405 nm was then measured and the percent inhibition of trypsin activity was calculated from $OD_{405nm}$ values in the absence and presence of a compound. Results in Table 1 (FIG. 2($a$)) showed that the compounds 1 and 2 (structures shown above) do not inhibit trypsin activity.

See also FIG. 3 showing percent inhibition of factor Xa and factor VIIa activity using 83 µM compound 1 or compound 2. FIG. 3 also shows percent inhibition of thrombin activity at 63 µM compound 1 or compound 2. Also shown in the figure is percent inhibition of trypsin activity at 71 µM compound 1 or compound 2.

EXAMPLE 4

Effects of TF Antagonists on FX Activation Catalyzed by RVV, FIXa, and FVIIa

In addition to TF/VIIa complex, RVV, FIXa, and FVIIa are also able to activate FX in vitro. The following assays were conducted to examine the effects of 1 and 2 (structures shown above) on FX activation catalyzed by RVV, FIXa, and VIIa. Data from these assays will help understand where these compounds may bind and the inhibitory mechanism.

A. RVV-dependent FX Activation

45 µl of RVV (0.1 nM) was added into each well of a 96-well plate that contains 5 µl of diluted DMSO (or buffer) or compound, then mixed and incubated at 37° C. for 15 minutes. Then 10 µl of FX (180 nM) was added and incubated for 15 minutes at 37° C. After adding 10 µl of EDTA (400 mM) and 10 µl of Spectrozyme FXa (5 mM), the reaction was incubated for 20 minutes at 37° C. Absorbance at 405 nm was then measured following addition of 20 µl of 50% acetic acid. The percent inhibition of RVV-dependent FX activation was calculated from $OD_{405nm}$ values in the absence and presence of a compound. The data shown in Table 2 (FIG. 2($b$)) indicated that the compounds 1 and 2 (structures shown above) do not inhibit RVV catalytic activity, and they do not bind to the cleavage site of FX. It has been established independently that all FX-activating enzymes (TF/VIIa, FVIIa, FIXa, and RVV) cleave the same site on FX.

B. FIXa-dependent FX Activation assay:

FIX was first converted to FIXa by TF/VIIa in the absence of compound. This was done in a 50-ml tube. After incubating TF/VIIa (0.67 nM, 10 ml) at 37° C. for 15 minutes, FIX (300 nM, 0.123 ml) was added and incubated at 37° C. for 30 minutes.

Then 1.54 ml of EDTA (400 mM) was added to stop the FIX activation. Then 65 µl of the above FIXa sample was transferred into wells of a 96-well plate that contain 5 µl of diluted DMSO (or buffer) or compound (in diluted DMSO or buffer). Ten µl of FX (1000 nM), 10 µl of polylysine (300 nM), and 10 µl of Spectrozyme FXa (5 mM) were added to each well and incubate at 37° C. until an $OD_{405nm}$ value of 0.8 was reached. Absorbance at 405 nm was then measured following addition of 20 µl of 50% acetic acid. The percent inhibition of FIXa activity was calculated from $OD_{405nm}$ values in the absence and presence of a compound. Again, compounds 1 and 2 do not inhibit FIXa activity, nor do they bind to FX in such a way that FX can not be activated by FIXa (Table 2, FIG. 2(b)).

C. FVIIa-dependent FX Activation:

FVIIa alone in the presence of phospholipids and calcium is also able to activate FX, although at a very low rate. This experiment was designed to examine whether compounds 1 and 2 inhibit FVIIa-dependent FX activation if TF is omitted. Inhibition of FVIIa-dependent-FX activation means that the two compounds may bind to FVIIa, while no inhibition indicates that the two compounds will not bind to FVIIa or FX. This assay was done at relatively high FVIIa concentrations. Six microliters of compound 1 (1 mM in 10% DMSO) or 10% DMSO was mixed with 40 $\mu$l of 25 mM HEPES-NaOH, 5 mM $CaCl_2$, 150 mM NaCl, 0.1% BSA, pH 7.5 containing phosphatidylcholine (0.07 mg/ml) and phosphatidylserine (0.03 mg/ml). Then 4 $\mu$l of FVIIa (1.5 $\mu$M) and 10 $\mu$l of FX (180 nM) were added and mixed. The mixture was incubated for 1 hour at 37° C. Then 10 $\mu$l of EDTA (400 mM) was added to stop FVII activity by removing the calcium required for factor VII activity. Then 10 $\mu$l of FXa substrate S-2765 (3.2 mM) was added to measure the FXa activity generated by FVIIa. After 16 minutes incubation at 37° C., 20 $\mu$l of 50% acetic acid was added to quench the reaction. Absorbance at 405 nm was read and the percent inhibition of FVIIa-dependent FX activation was calculated from $OD_{405nm}$ values in the absence and presence of compound 1. The data shown in Table 2 (FIG. 2(b)) indicates that compound 1 does not inhibit FVIIa-dependent FX activation, indicating that it does not bind to FVIIa or to FX.

D. Inhibition of TF/VIIa-dependent FX Activation

To determine the inhibition of TF/VIIa-dependent FX activation by compounds 1 and 2 at lower concentrations, compounds in DMSO were diluted with 10 mM HEPES-NaOH, pH 7.5 and the assays were then performed as previously described in the primary screening method. Table 3 (FIG. 2(c)) is the titration results of TF/VIIa-dependent FX activation for compounds 1 and 2. In some experiments, both compounds were dissolved in 0.1 M NaOH, then diluted by water to 16.5 mM NaOH. From the data in Table 3, the compounds 1 and 2 (structures shown above) inhibit TF/VIIa-dependent FX activation, with $IC_{50}$ (inhibitor concentrations at which 50% of TF/VIIa-dependent FX activation is inhibited) values of 19.0 $\mu$M for compound 1 and 9.7 $\mu$M for 2.

E. Inhibition of TF/VIIa-dependent FIX Activation

TF/VIIa is not only able to activate FX, but is also able to convert FIX to FIXa. To examine whether the two antagonists 1 and 2 were able to block FIX activation catalyzed by TF/VIIa. FIX activation experiment was conducted. To each well of a 96-well plate, 5 $\mu$l of diluted DMSO or compound was added, followed by 45 $\mu$l of TF/VIIa (0.67 nM). After mixing and incubating for 15 minutes at 37° C., 10 $\mu$l of FIX (300 nM) was added and incubated for 10 minutes at 37° C. 10 $\mu$l of EDTA (400 nM in 144 mM HEPES, 864 nM NaCl, 0.576% BSA, pH adjusted to 7.5) was added, followed by addition of 10 $\mu$l of FX (1000 nM), 10 $\mu$l of polylysine, and 10 $\mu$l of Spectrozyme FXa (6 mM). After 3 hour incubation at 37° C., absorbance at 405 nm was measured following addition of 20 $\mu$l of 50% acetic acid. The percent inhibition of TF/VIIa-dependent FIX activation was calculated from $OD_{405nm}$ values in the absence and presence of a compound. The data in Table 4 (FIG. 2(d)) shows that compounds 1 and 2 (structure shown above) inhibit TF/VIIa-dependent FIX activation similarly as seen in TF/VIIa-dependent FX activation.

EXAMPLE 5

Inhibition Mechanism of TF Antagonists

Figure 6:
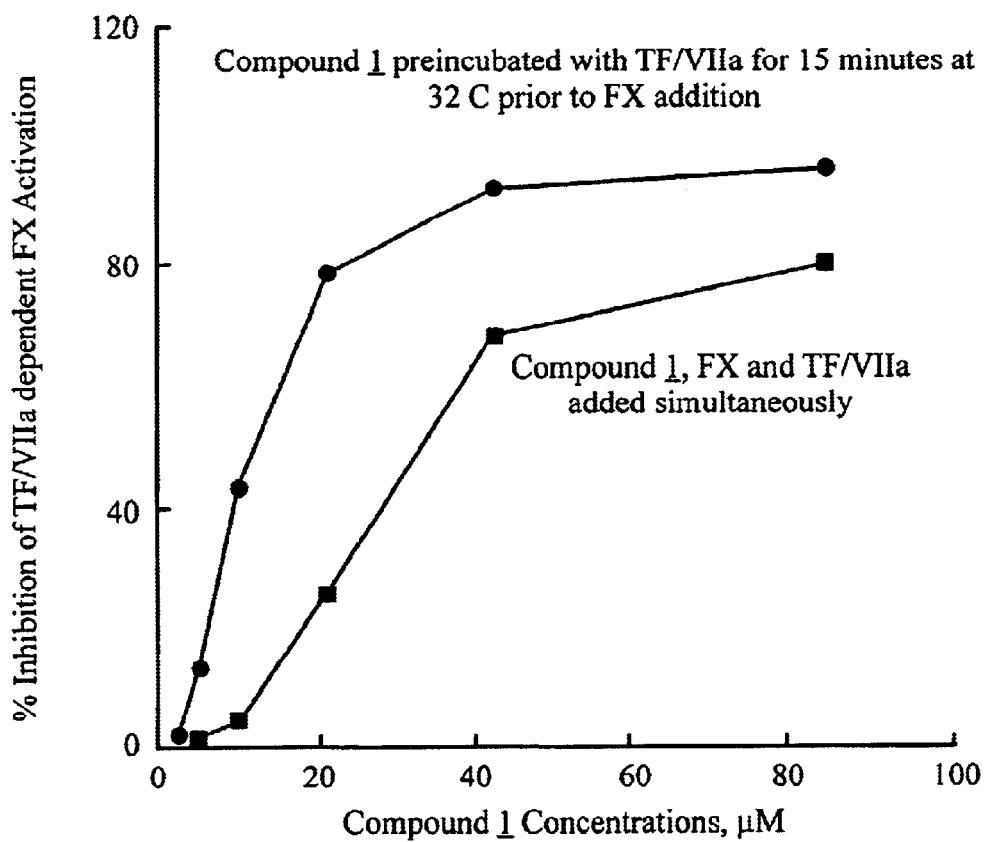
FIG. 6 is a graph showing inhibition of TF/VIIa-dependent activation by compound 1. FX concentration was 30 nM in the assay.
Figure 7:
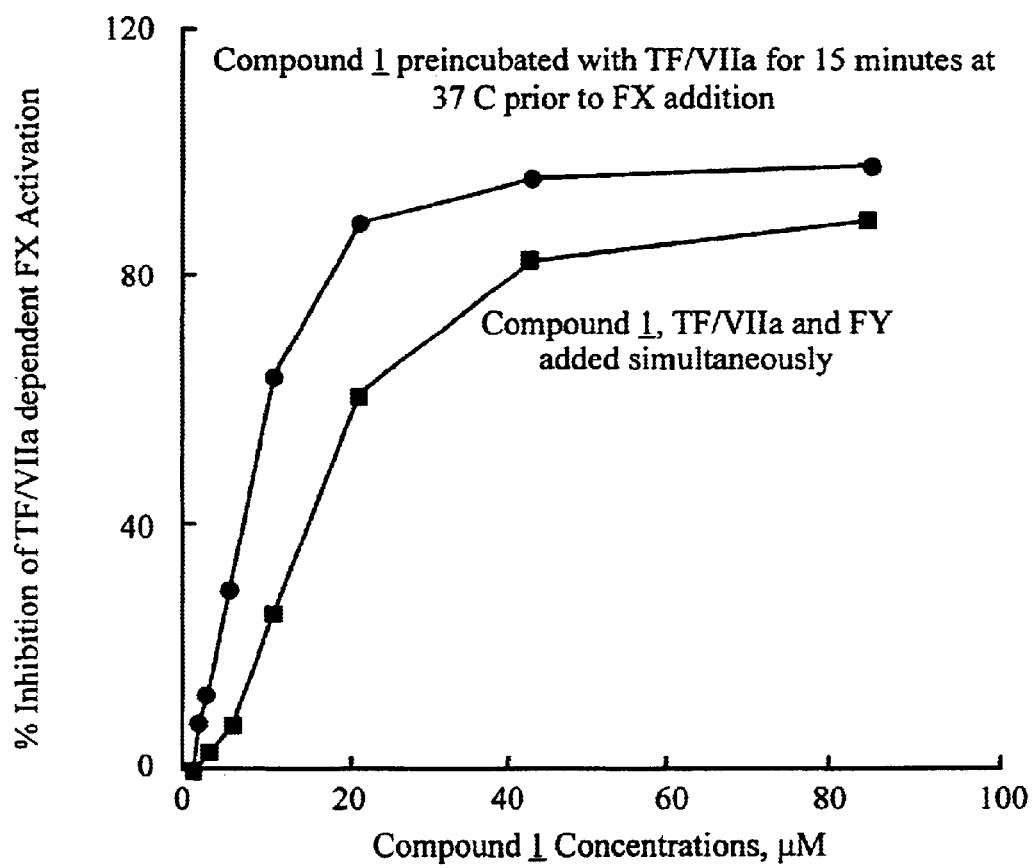
FIG. 7 is a graph showing inhibition of TF/VIIa-dependent FX activation by compound 1. FX concentration was 5 nM in the assay.

Examples 3 and 4 above showed that the compounds of the invention are TF specific antagonists. To elucidate the inhibition mechanism of TF antagonists, the following experiments were conducted. Compound 1 was titrated from 0 to 84 $\mu$M under two assay conditions using two different FX concentrations. Under one condition, compound 1 was preincubated with TF/VIIa for 15 minutes at 37° C. prior to addition of FX. Under another condition, TF/VIIa, FX, and compound 1 were added and mixed simultaneously. One set of experiments was conducted at 5 nM FX, the other set at 30 nM FX. From results shown in FIGS. 6 and 7, $IC_{50}$ values from preincubation experiments are somewhat lower than those from the simultaneous addition expeiments (compare 8.3 $\mu$M with 18.1 $\mu$M when FX was 5 nM, and 12.5 $\mu$M with 33.2 $\mu$M when FX was 30 nM). Furthermore, $IC_{50}$ values increased with increasing FX concentration. For example, $IC_{50}$ values increased from 8.3 $\mu$M and 18.1 $\mu$M to 12.5 $\mu$M and 33.2 $\mu$M, respectively, when FX increased from 5 nM to 30 nM under the two assay conditions. These data suggest that compound 1 compete each other for binding to TF.

Further kinetic analysis of TF-VIIa-dependent FX activation showed that Compound 1 significantly increased the apparent Km values for FX substrate (see FIG. 5). This indicates that (1), compound 1 is a competitive inhibitor for TF/VIIa complex, (2), the binding of compound 1 to TF/VIIa blocks FX binding to TF/VIIa complex. The binding of compound 1 to TF (243 form lipidated or 219 form unlipidated) also was directly observed by isothermal calorimetry analysis.

EXAMPLE 6

Effects of Compounds of the Invention in the Prothrombin Time (PT) Assay

The prothrombin time (PT) test was conducted as follows:

The PT assay was performed at 37° C. with an Electra 800 (Medical Automation, Inc.). The PT reaction was initiated by adding 0.2 ml of lipidated recombinant human tissue factor into 0.105 ml of human plasma (Ci-Trol Control Level I, from VWR, Cat. No. 68100-336). 1 ml purified water was added to each vial of Ci-Trol and mixed to solubilize. If more than one vial was used, it was often helpful to combine them into one container. 5 $\mu$l of DMSO or 5 $\mu$l of compound was added to each well of the twin-well cuvette that contains 0.1 ml of Ci-Trol. It is helpful to use a pipet with 0.1 ml tip to mix each well. Make sure no air bubbles are in the well. Following mixing the compound (or DMSO) with plasma (Ci-Trol), 0.2 ml of lipidated reocombinant tissue factor (1–3 nM) is added to the plasma and clotting times were measured within 10 min. The data in FIG. 4 indicate compounds 1 and 2 prolonged TF-initiated PT times significantly.

The invention has been described in detail with reference to preferred embodiments thereof. However, it will be appreciated that those skilled in the art, upon consideration of the disclosure, may make modification and improvements within the spirit and scope of the invention.

What is claimed is:

1. A method for treating a mammal suffering from a blood coagulation disorder, comprising administering to the mammal a therapeutically effective amount of a compound of the following Formula I:

$$Ar—(CXY)_m—(Het)_{0 \text{ or } 1}—(CX'Y')_n—C(Z)_p—(PO_3)_{3-p} \qquad I$$

wherein Ar is optionally substituted carbocyclic aryl or optionally substituted heteroaryl;

Het is optionally substituted N, O, S, S(O) or S(O$_2$);

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; or alkylamino;

m and n each is independently an integer of from 0 to 4; p is 1 or 2; and pharmaceutically acceptable salts thereof.

2. A method for treating a mammal suffering from a blood coagulation disorder, comprising administering to the mammal a therapeutically effective amount of a compound of the following Formula I:

$$Ar—(CXY)_m—(Het)_{0 \text{ or } 1}—(CX'Y')_n—C(Z)_p—(PO_3)_{3-p} \qquad I$$

wherein Ar is optionally substituted heteroaryl;

Het is optionally substituted N, O, S, S(O) or S(O$_2$);

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; or optionally substituted alkylamino;

m and n each is independently an integer of from 0 to 4; p is 1 or 2; and pharmaceutically acceptable salts thereof.

3. A method for treating a mammal suffering from a thrombosis, comprising administering to the mammal a therapeutically effective amount of a compound of the following Formula I:

$$Ar—(CXY)_m—(Het)_{0 \text{ or } 1}—(CX'Y')_n—C(Z)_p—(PO_3)_{3-p} \qquad I$$

wherein Ar is optionally substituted carbocyclic aryl or optionally substituted heteroaryl;

Het is optionally substituted N, O, S, S(O) or S(O$_2$);

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; or optionally substituted alkylamino;

m and n each is independently an integer of from 0 to 4; p is 1 or 2; and pharmaceutically acceptable salts thereof.

4. A method for treating a mammal suffering from a blood coagulation disorder, comprising administering to the mammal a therapeutically effective amount of a compound of the following Formula II:

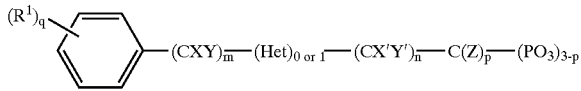

wherein Het is optionally substituted N, O, S, S(O) or S(O$_2$);

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; or optionally substituted alkylamino;

each R$^1$ is independently halogen; amino; hydroxy; nitro; carboxy; sulfhydryl; optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; alkylamino; optionally substituted alkanoyl; optionally substituted carbocyclic aryl; or optionally substituted aralkyl;

m and n each is independently an integer of from 0 to 4; p is 1 or 2; q is an integer of from 0 to 5; and pharmaceutically acceptable salts thereof.

5. A method for treating a mammal suffering from a thrombosis, comprising administering to the mammal a therapeutically effective amount of a compound of the following Formula II:

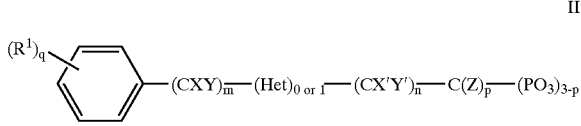

wherein Het is optionally substituted N, O, S, S(O) or S(O$_2$);

each X, each Y, each X', each Y' and each Z are each independently hydrogen; halogen; hydroxyl; sulfhydryl; amino; optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; or optionally substituted alkylamino;

each R$^1$ is independently halogen; amino; hydroxy; nitro; carboxy; sulfhydryl; optionally substituted alkyl; optionally substituted alkenyl; optionally substituted alkynyl; optionally substituted alkoxy; optionally substituted alkylthio; optionally substituted alkylsulfinyl; optionally substituted alkylsulfonyl; optionally substituted alkylamino; optionally substituted alkanoyl; optionally substituted carbocyclic aryl; or optionally substituted aralkyl;

m and n each is independently an integer of from 0 to 4; p is 1 or 2; q is an integer of from 0 to 5; and pharmaceutically acceptable salts thereof.

* * * * *

UNITED STATES PATENT AND TRADEMARK OFFICE
CERTIFICATE OF CORRECTION

PATENT NO. : 6,828,312 B2  Page 1 of 1
APPLICATION NO. : 09/406269
DATED : December 7, 2004
INVENTOR(S) : Jiao et al.

It is certified that error appears in the above-identified patent and that said Letters Patent is hereby corrected as shown below:

In column 12, at line 50, replace " 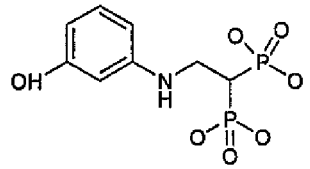 " with -- 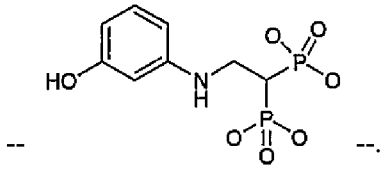 --.

In column 13, at line 3, replace " 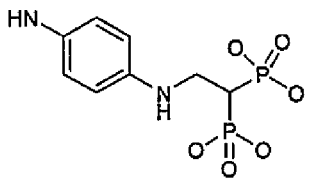 " with -- 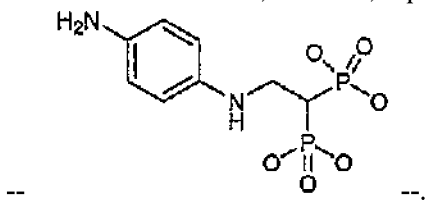 --.

Signed and Sealed this

Twenty-first Day of August, 2007

JON W. DUDAS
*Director of the United States Patent and Trademark Office*